(12) United States Patent
Kamal et al.

(10) Patent No.: US 7,465,724 B2
(45) Date of Patent: Dec. 16, 2008

(54) BIS-PYRROLO[2,1-C][1,4]BENZODIAZEPINE-ANTHRAQUINONE CONJUGATES AND A PROCESS FOR THE PREPARATION THEREOF

(75) Inventors: Ahmed Kamal, Hyderabad (IN); Rondla Ramu, Hyderabad (IN); Gollapalli Bhasker Ramesh Khanna, Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 11/705,660

(22) Filed: Feb. 12, 2007

(65) Prior Publication Data

US 2007/0259858 A1    Nov. 8, 2007

(30) Foreign Application Priority Data

Feb. 13, 2006    (IN) .......................... 383/DEL/2006

(51) Int. Cl.
C07D 405/14    (2006.01)
A61K 31/551    (2006.01)
(52) U.S. Cl. ...................................... 514/220; 540/496
(58) Field of Classification Search ................ 540/496; 514/220
See application file for complete search history.

(56) References Cited

U.S. PATENT DOCUMENTS 7,312,210 B2 * 12/2007 Kamal et al. ................ 514/220

\* cited by examiner

*Primary Examiner*—Bruck Kifle
(74) *Attorney, Agent, or Firm*—Daniel A. Monaco; Drinker Biddle & Reath LLP

(57) ABSTRACT

The present invention provides novel bis-pyrrolo[2,1-c][1,4] benzodiazepine-anthraquinone conjugates of general formula V, useful as potential antitumour agents against human cancer cell lines. The present invention further provides a process for the preparation of novel bis-pyrrolo[2,1-c][1,4] benzodiazepine-anthraquinone conjugates of general formula V.

Figure 1:
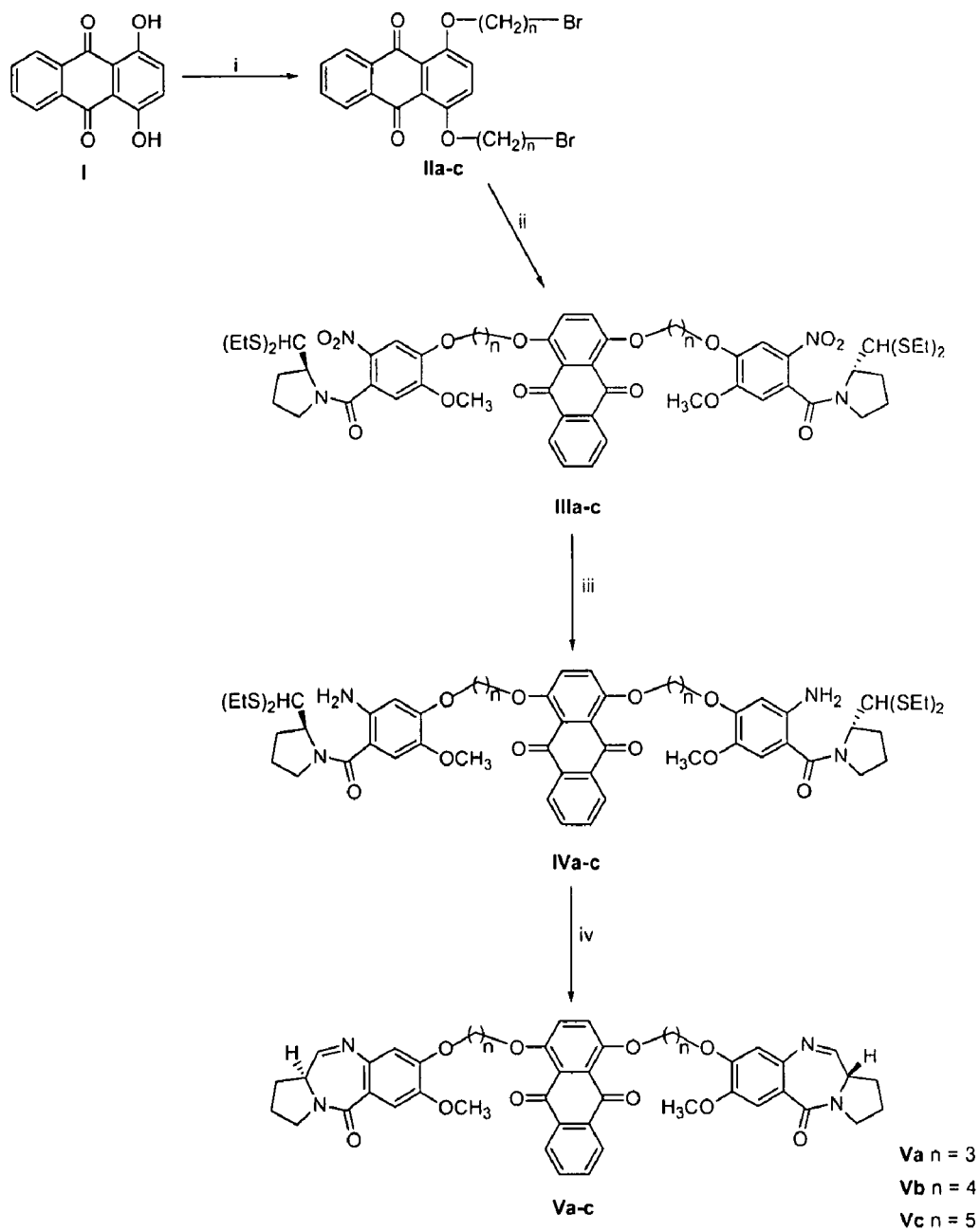

Formula V wherein n=3, 4, or 5.

11 Claims, 1 Drawing Sheet

Reagents and conditions: (i) Dibromoalkane, $K_2CO_3$, acetone, reflux, 2 (2S)-N-[4-hydroxy-5-methoxy-2-nitrobenzoyl]pyrrolidine-2-carboxaldehyde diethyl thioacetal, $K_2CO_3$, acetonitrile, reflux, 24h; (iii) $SnCl_2 \cdot 2H_2O$, MeOH, reflux, 4h; (iv) $HgCl_2$ $CH_3CN/H_2O$, rt, 12h.

BIS-PYRROLO[2,1-C][1,4]BENZODIAZEPINE-ANTHRAQUINONE CONJUGATES AND A PROCESS FOR THE PREPARATION THEREOF

FIELD OF THE INVENTION

The present invention relates to a novel bis-pyrrolo[2,1-c][1,4]benzodiazepine-anthraquinone conjugates and a process for the preparation thereof. More particularly, it relates to a process for the preparation of novel bis-pyrrolo[2,1-c][1,4]benzodiazepine-anthraquinone hybrids as potential antitumour agents.

The present invention particularly relates to the synthesis of pyrrolo[2,1-c][1,4]benzodiazepine-anthraquinone hybrids linked through alkanediyldioxy bridge with linkers of varying lengths as possible anticancer agents. The structural formula of novel bis-pyrrolo[2,1-c][1,4]benzodiazepine-anthraquinone hybrids (Va-c) is as follows,

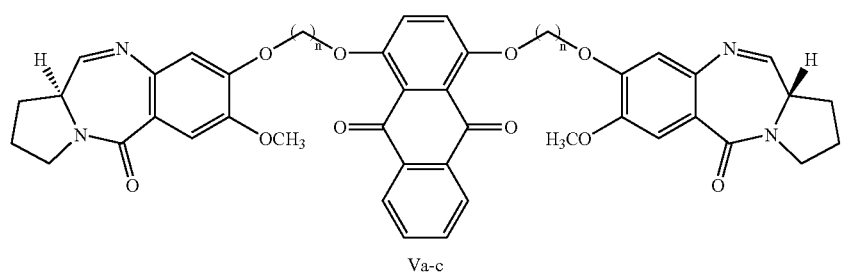

Formula Va-c

Va-c wherein n=3, 4, 5.

BACKGROUND OF THE INVENTION

The pyrrolo[2,1-c][1,4]benzodiazepines are a family of DNA interactive antitumour antibiotics derived from Streptomyces species. Examples of naturally occurring pyrrolo[2,1-c][1,4]benzodiazepines include anthramycin, tomaymycin, sibiromycin and DC-81. These compounds show their biological activity through covalent binding via their N10-C11 imine/carbinol amine moiety to the C2-amine position of a guanine residue within the minor groove of DNA giving rise to the preference for Pu-G-Pu sequences. (Kunimoto, S.; Masuda, T.; Kanbayashi, N.; Hamada, M.; Naganawa, H.; Miyamoto, M.; Takeuchi, T and Unezawa, H. *J. Antibiot.,* 1980, 33, 665.; Kohn, K. W. and Speous, C. L. *J. Mol. Biol.,* 1970, 91, 551.; Hurley, L. H.; Gairpla, C. and Zmijewski, M. *Biochem. Biophy. Acta.,* 1977, 475, 521.; Kaplan, D. J. and Hurley, L. H. *Biochemistry,* 1981, 20, 7572.) The molecules have a right-handed twist, when viewed from the C-ring towards the A-ring. This enables the PBD to mirror the curvature of B-form DNA and maintain isohelical contact with the walls and floor of the minor groove.

In the last few years a growing interest has been shown in the development of new pyrrolo[2,1-c][1,4]benzodiazepine hybrids. Many PBD conjugates have been synthesized and investigated for their anticancer activity (Thurston, D. E.; Morris, S. J.; Hartley, J. A. *Chem. Commun.* 1996, 563.; Damayanthi, Y.; Reddy, B. S. P.; Lown, J. W. *J. Org. Chem.* 1999, 64, 290.; Kamal, A.; Reddy, B. S. N.; Reddy, G. S. K.; Ramesh, G *Bioorg. Med. Chem. Lett.* 2002, 12,1933, Kamal, A.; Reddy, B. S. N.; Reddy Indian patent application No.209/DEL/2000). Recently C-8 linked PBD dimers with C2/C2 exo-unsaturation have been designed and synthesized (Gregson, S. J.; Howard, P. W.; Hartley, J. A.; Brooks, N. A.; Adam, L. J.; Jenkins, T. C.; Kelland, L. R. and Thurston, D. E., *J. Med. Chem.* 2001, 44, 737). Also, non cross-linking mixed imine-amide PBD dimers have been synthesized that have significant DNA binding ability and potent antitumor activity (Kamal, A.; Ramesh, G.; Laxman, N.; Ramulu, P.; Srinivas, O.; Neelima, K.; Kondapi, A. K.; Srinu, V. B.; Nagarajaram, H. M. *J. Med. Chem.* 2002, 45, 4679).

During earlier studies in this laboratory anthraquinone has been linked through its amino functionality to the C8 position of the A-ring of PBDs which have shown promising anticancer activity (Kamal, A.; Ramu, R.; Khanna, G. B. R.; *Bioorg. Med. Chem. Lett.* 2004, 14, 4907, Kamal, A.; Ramu, R.; Khanna, G. B. R. PCT Patent Appl. No. PCT/IN04/00212, U.S. patent application Ser. No.11/024,240).

However, in the present invention the two pbd units have been joined to the 1,4-positions of the anthraquinone through their a-c8 positions via alkanediyldioxy bridge with linkers of varying lengths provide novel pyrrolo[2,1-c][1,4]benzodiazepines useful as anticancer agents. It also provides a process for the preparation of novel pyrrolo[2,1-c][1,4]benzodiazepines useful as antitumor agents.

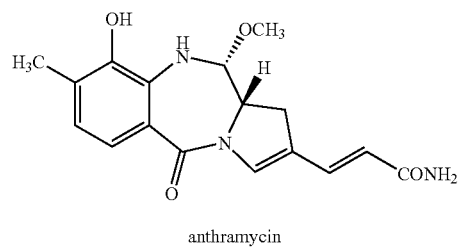

anthramycin

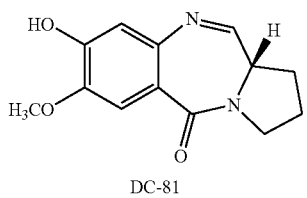

DC-81

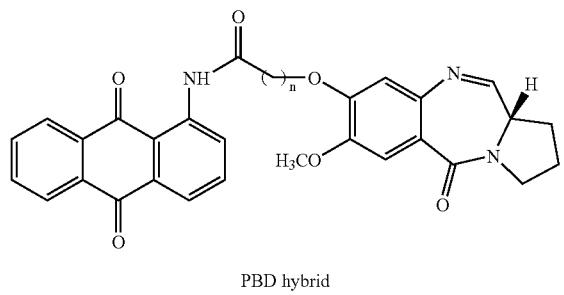

PBD hybrid

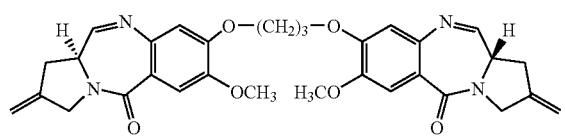

SJG-136

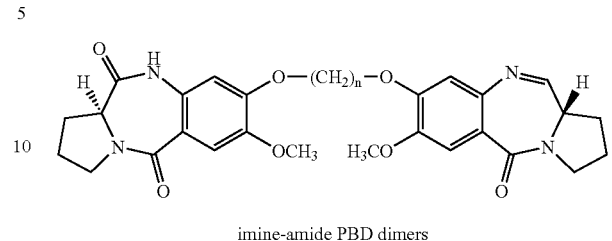

imine-amide PBD dimers

OBJECTIVES OF THE INVENTION

The main object of the present invention is to provide novel pyrrolo[2,1-c][1,4]benzodiazepines anthraquinone conjugates.

Yet another object is to provide novel pyrrolo[2,1-c][1,4] benzodiazepines anthraquinone conjugates, which are useful as anti tumour agents against human cancer cell lines.

Yet another object of the invention is to provide a process for the preparation of novel pyrrolo[2,1-c][1,4]benzodiazepines anthraquinone conjugates.

SUMMARY OF THE INVENTION

Accordingly the present invention provides a novel bis-pyrrolo[2,1-c][1,4]benzodiazepine-anthraquinone conjugate of general formula V,

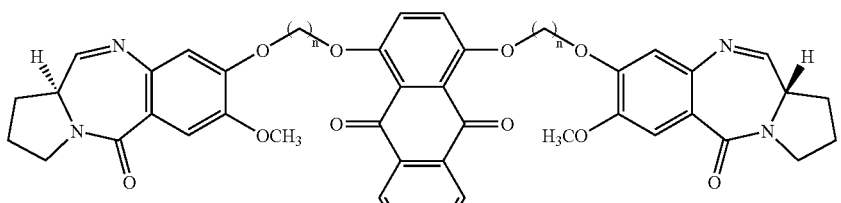

Va-c wherein n=3; (va) or 4; (vb), or 5; (vc).

In an embodiment of the present invention the Novel bis-pyrrolo[2,1-c][1,4]benzodiazepine-anthraquinone conjugate of formula V is representative by the group of the following compounds:
1,4-Bis-{3-[7-methoxy-8-oxy-(11aS)-1,2,3,11a tetrahydro-5H-pyrrolo [2,1-c][1,4]-benzodiazepin-5-one] propyloxy}anthracene-9,10-dione (Va);
1,4-Bis-{4-[7-methoxy-8-oxy-(11aS)-1,2,3,11a tetrahydro-5H-pyrrolo [2,1-c][1,4]benzodiazepin-5-one] butyloxy}anthracene-9,10-dione (Vb) and
1,4-Bis-{5-[7-methoxy-8-oxy-(11aS)-1,2,3,11a tetrahydro-5H-pyrrolo [2,1-c][1,4]benzodiazepin-5-one] pentyloxy}anthracene-9,10-dione (Vc)

In yet another embodiment wherein the structural formula of the representative compounds are:

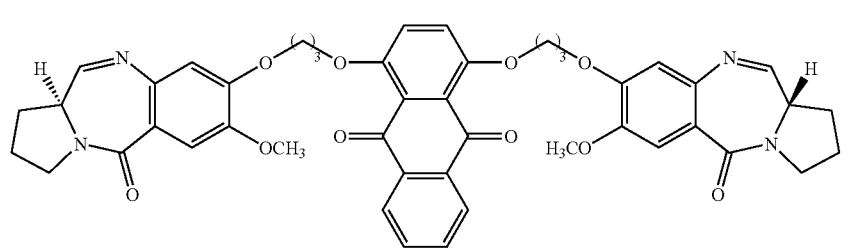

formula Va

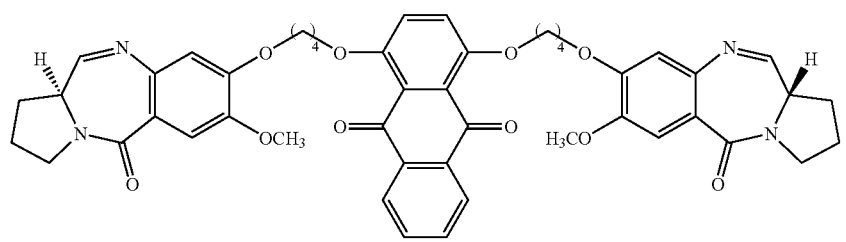

formula Vb

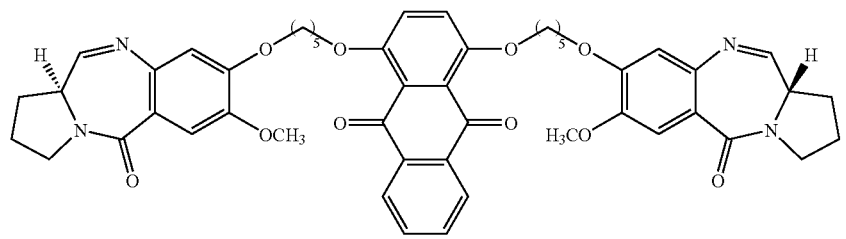

formula Vc

In yet another embodiment the Novel bis-pyrrolo[2,1-c][1,4]benzodiazepine-anthraquinone exhibits invitro anticancer/antitumour activity against human cancer cell lines selected from lung, cervix, breast, colon, prostate and ovary cell lines.

In yet another embodiment the concentration of the compound bis-pyrrolo[2,1-c][1,4]benzodiazepine-anthraquinone (Va-c) used for invitro activity against HoP62 for IC50 is in the range of 0.1 to 1.4 μM, for an exposure period of at least 48 hrs.

In yet another embodiment the concentration of the compound bis-pyrrolo[2,1-c][1,4]benzodiazepine-anthraquinone (Va-c) used for invitro anti tumour activity activity against SiHa for IC50 is in the range of 0.8 to 9.0 μM, for an exposure period of atleast 48 hrs.

In yet another embodiment the concentration of the compound bis-pyrrolo[2,1-c][1,4]benzodiazepine-anthraquinone (Va-c) used for invitro anti tumour activity activity against MCF7 for IC50 is in the range of 0.6 to 9.0 μM, for an exposure period of atleast 48 hrs.

In yet another embodiment the concentration of the compound bis-pyrrolo[2,1-c][1,4]benzodiazepine-anthraquinone (Va-c) used for invitro anti tumour activity activity against Colo205 for IC50 is in the range of 1.0 to 10.0 μM, for an exposure period of atleast 48 hrs.

In yet another embodiment the concentration of the compound bis-pyrrolo[2,1-c][1,4]benzodiazepine-anthraquinone (Va-c) used for invitro anti tumour activity activity against PC3 for IC50 is in the range of 1.0 to 1.4 μM for an exposure period of at least 48 hrs.

In yet another embodiment the concentration of the compound bis-pyrrolo[2,1-c][1,4]benzodiazepine-anthraquinone (Va-c) used for invitro anti tumour activity activity against ZR-75-1 for IC50 is in the range of 0.5 to 1.5 μM for an exposure period of at least 48 hrs.

In yet another embodiment the concentration of the compound bis-pyrrolo[2,1-c][1,4]benzodiazepine-anthraquinone (Va-c)used for invitro anti tumour activity activity against A2780 is in the range of 0.6to 10.0 μM for an exposure period of at least 48 hrs.

The present invention further provides a pharmaceutical composition comprising novel bis-pyrrolo[2,1-c][1,4]benzodiazepine-anthraquinone, conjugates, its derivatives, analogues salts or mixture thereof optionally with pharmaceutically acceptable carriers, adjuvants and additives.

In yet another embodiment the novel bis-pyrrolo[2,1-c][1,4]benzodiazepine-anthraquinone conjugates used in pharmaceutical composition has a general formula V,

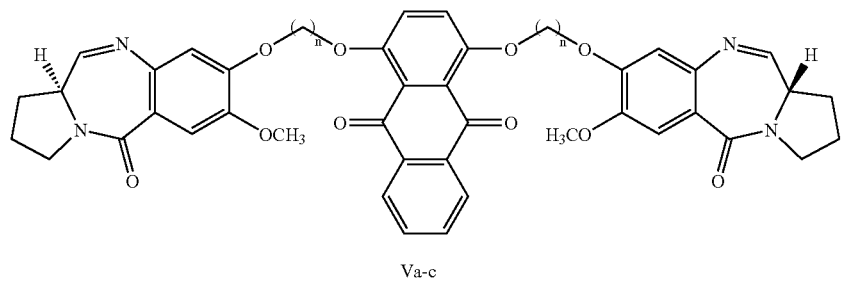

Va-c wherein n=3; (Va) or 4; (Vb), or 5; (Vc).

In yet another embodiment pharmaceutical composition exhibits invitro anticancer/anti tumour activity against human cancer cell lines selected from lung, cervix, breast, colon, prostate and ovary cell lines.

The present invention further provides a process (FIG. 1) for the preparation of novel bis-pyrrolo[2,1-c][1,4]benzodiazepine-anthraquinone conjugates of formula V, the said process comprising the steps of:

a. reacting 1,4-dihydroxy anthraquinone of formula I with dibromoalkanes, in an aprotic water miscible organic solvent, in the presence of a mild inorganic base, at refluxing temperature, for a period of about 24 hours, followed by the removal of inorganic base by filtration and removing the organic solvent by evaporation under reduced pressure, to obtain the 1,4-bis-(3-bromo alkoxy)-anthracene-9,10-dione of formula IIa-c,

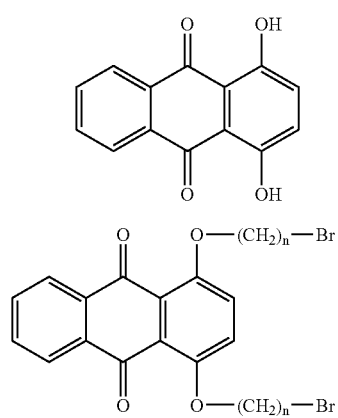

b. reacting 1,4-bis-(3-bromo alkoxy)anthracene-9,10-dione of formula IIa-c with (2S)-n-[4-hydroxy-5-methoxy-2-nitrobenzoyl]pyrrolidine-2-carbox aldehyde diethyl thioacetal in a dry organic solvent, in the presence of mild inorganic base, at refluxing temperature, for a period of about 24 hours, followed by the removal of inorganic base by filtration and removing the organic solvent by evaporation, under reduced pressure, to obtain the desired product 1,4-bis-{n-[(2S)-N-(4-oxy-5-methoxy-2-nitrobenzoyl)pyrrolidine-2-carboxaldehyde diethyl thioacetal]alkyloxy}-anthracene-9,10-dione of formula IIIa-c.

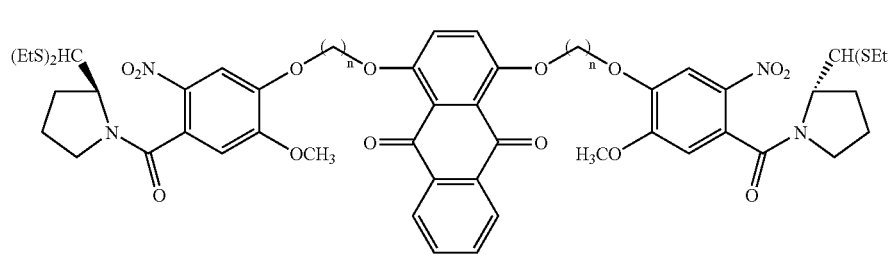

IIIa-c wherein n=3; (IIIa) or 4; (IIIb), or 5; (IIIc)

c. reducing the compound 1,4-bis-{n-[(2S)-N-(4-oxy-5-methoxy-2-nitrobenzoyl)pyrrolidine-2-carboxaldehyde diethyl thioacetal]alkyloxy}-anthracene-9,10-dione of formula III with tin chloride, in an alcoholic solvent, under reflux, for a period of about 4 hours, cooling the resultant reaction reaction mixture to a temperature of 20-25° C., and removing the excess alcohol by evaporation and adjusting the residue to a pH of about 8 with an inorganic base, followed by extraction with ethyl acetate and washing the combined organic phase with brine solution and evaporating the solvent to obtain the desired compound 1,4-bis-{n-[(2S)-N-(4-oxy-5-methoxy-2-aminobenzoyl)pyrrolidine-2-carboxaldehyde diethyl thioacetal]alkyloxy}anthracene-9,10-dione of formula IVa-c.

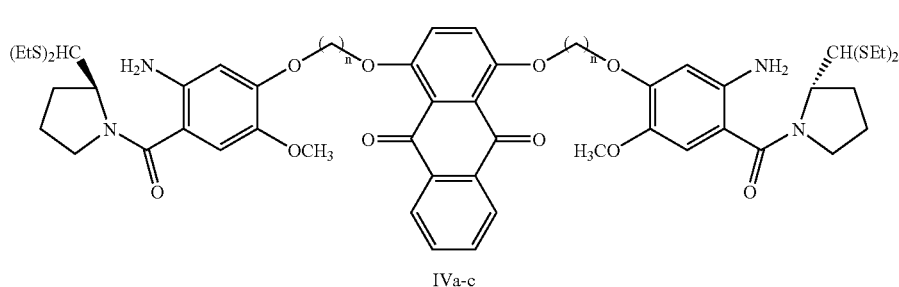

formula IV

IVa-c wherein n=3; (IVa) or 4; (IVb), or 5; (IVc)

d. reacting amino thioacetal 1,4-bis-{n-[(2S)-N-(4-oxy-5-methoxy-2-aminobenzoyl)pyrrolidine-2-carboxaldehyde diethyl thioacetal]alkyloxy}-anthracene-9,10-dione of formula IVa-c with mercuric chloride in a mixture of water and acetonitrile, in the presence of and calcium carbonate, under stirring, for a period of about 8-10 hours, at a temperature in the range of 25-30° C. and diluting it with ethyl acetate, followed by filtration and extraction of the organic supernatant with ethyl acetate, washing the resultant organic phase with sodium bi carbonate and brine, and evaporating the organic layer, followed by purification by known method to obtain the desired product of formula Va-c.

In an embodiment of the present invention the mild inorganic base used in steps (a) & (b) is potassium bicarbonate.

In yet another embodiment the novel bis-pyrrolo[2,1-c][1,4]benzodiazepine-anthraquinone of formula V obtained is represented by the group of the following compounds:

1,4-Bis-{3-[7-methoxy-8-oxy-(11aS)-1,2,3,11a tetrahydro-5H-pyrrolo[2,1-c][1,4]-benzodiazepin-5-one]propyloxy}anthracene-9,10-dione(Va), 1,4-Bis-{4-[7-methoxy-8-oxy-(11aS)-1,2,3,11a tetrahydro-5H-pyrrolo[2,1-c][1,4]benzodiazepin-5-one]butyloxy}anthracene-9,10-dione (Vb) and 1,4-Bis-{5-[7-methoxy-8-oxy-(11aS)-1,2,3,11a tetrahydro-5H-pyrrolo[2,1-c][1,4]benzodiazepin-5-one]pentyloxy}anthracene-9,10-dione (Vc).

In yet another embodiment the bromoalkane used in step (a) is selected from the group consisting of 1,3 dibromopropane, 1,3 dibromobutane, and 1,3 dibromopentane.

In yet another embodiment the organic solvent used in step (a) is selected from acetone, and acetonitrile.

In yet another embodiment the compound of formula IIa-c used in step (b) is selected from the group consisting of 1,4-bis-(3-bromo propyloxy)-anthracene-9,10-dione, 1,4-bis-(3-bromobutyloxy)-anthracene-9,10-dione and 1,4-bis-(3-bromo pentyloxy)-anthracene-9,10-dione.

In yet another embodiment the organic solvent used in step (b) is selected from acetonitrile, acetone and DMF.

In yet another embodiment the compound of formula IIa-c used in step (c) is selected from the group consisting of 1,4-bis-{3-[(2S)-N-(4-oxy-5-methoxy-2-nitrobenzoyl)pyrrolidine-2-carboxaldehyde diethyl thioacetal]propyloxy}anthracene-9,10-dione (IIIa), 1,4-bis-{4-[(2S)-N-(4-oxy-5-methoxy-2-nitrobenzoyl)pyrrolidine-2-carboxaldehyde diethyl thioacetal]butyloxy}anthracene-9,10-dione (IIIb) and 1,4-bis-{5-[(2S)-N-(4-oxy-5-methoxy-2-nitrobenzoyl)pyrrolidine-2-carboxaldehyde diethyl thioacetal]pentyloxy}-anthracene-9,10-dione (IIIc).

In yet another embodiment the alcohol used in step (c) is selected from methanol and ethanol.

In yet another embodiment the compound of formula IVa-c used in step (d) is selected from 1,4-bis-{3-[(2S)-N-(4-oxy-5-methoxy-2-aminobenzoyl)pyrrolidine-2-carboxaldehyde diethyl thioacetal]propyloxy}anthracene-9,10-dione (IVa), 1,4-bis-{4-[(2S)-N-(4-oxy-5-methoxy-2-aminobenzoyl)pyrrolidine-2-carboxaldehyde diethyl thioacetal]butyloxy}-anthracene-9,10-dione (IV b), and 1,4-bis-{5-[(2S)-N-(4-oxy-5-methoxy-2-aminobenzoyl)pyrrolidine-2-carboxaldehyde diethyl thioacetal]pentyloxy}-anthracene-9,10-dione (IVc).

In still another embodiment the novel bis-pyrrolo[2,1-c][1,4]benzodiazepine-anthraquinone conjugates of formula V exhibits an anti tumour activity against human cancer lines selected from the group consisting of lung, cervix, breast, colon, prostate and ovary cell lines.

DETAILED DESCRIPTION OF THE INVENTION

The present invention provides a process for the preparation of pyrrolo[2,1c][1,4]benzodiazepines anthraquinone-anthraquinone of formula V of the drawing accompanying the specification,

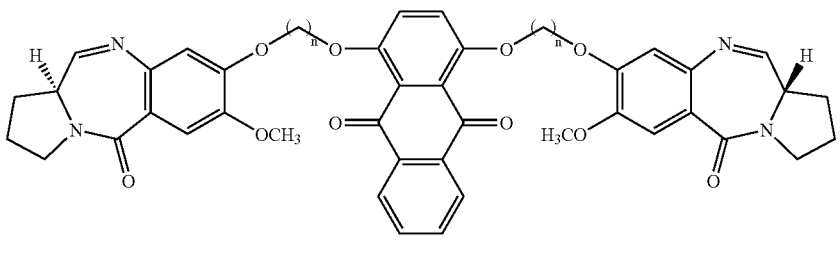

Va-c wherein n=3, 4 or 5.

The invention involves the reaction of 1,4-dihydroxy anthraquinone of formula I with dibromoalkanes in an aprotic water miscible organic solvent, in the presence of a mild inorganic base, at refluxing temperature, for a period of 24 h, isolating 1,4-bis-(n-bromo alkyloxy)-anthracene-9,10-dione of formula II and reacting the compound of formula IIa-c with (2S)-N-[4-hydroxy-5-methoxy-2-nitrobenzoyl]pyrrolidine-2-carboxaldehyde diethylthioacetal in presence of mild inorganic bases isolating compound of formula II, reducing it with $SnCl_2.2H_2O$ in presence of organic solvent at a reflux temperature, reacting the above amino compound of formula IV with known deprotecting agents in a conventional manner to get the novel pyrrol[2,1-c][1,4]benzodiazepine of formula V wherein 'n' are as stated above.

The precursor, (2S)-N-[4-hydroxy-5-methoxy-2-nitrobenzoyl]pyrrolidine-2-carboxaldehyde diethylthioacetal has been prepared by literature methods (Thurston, D. E.; Murthy, V. S.; Langley, D. R.; Jones, G. B. *Synthesis*, 1990, 81).

The representative compounds of formula V of present invention are given below:

1] 1,4-Bis-{3-[7-methoxy-8-oxy-(11aS)-1,2,3,11a tetrahydro-5H-pyrrolo [2,1-c][1,4]-benzodiazepin-5-one]propyloxy}anthacene-9,10-dione (Va)

2] 1,4-Bis-{4-[7-methoxy-8-oxy-(11aS)-1,2,3,11a tetrahydro-5H-pyrrolo [2,1-c][1,4]benzodiazepin-5-one]butyloxy}anthacene-9,10-dione (Vb)

3] 1,4-Bis-{5-[7-methoxy-8-oxy-(11aS)-1,2,3,11a tetrahydro-5H-pyrrolo [2,1-c][1,4]benzodiazepin-5-one]pentyloxy}anthacene-9,10-dione (Vb)

These new analogues of pyrrolo[2,1-c][1,4]benzodiazepine hybrids have shown promising anticancer activity in selected human cancer cell lines. The molecules synthesized are of immense biological significance with potential sequence selective DNA-binding property. This resulted in the design and synthesis of new congeners as illustrated in Scheme which comprises of
1. The ether linkage at C-8 position of DC-81 intermediates with anthraquinone moiety.
2. Refluxing the reaction mixture for 24-48 h.
3. Synthesis of C-8 linked PBD hybrids.
4. Purification by column chromatography using different solvents like ethyl acetate, hexane, dichloromethane and methanol.

The following examples are given by way of illustration and therefore should not be construed to limit the scope of the invention.

EXAMPLE 1

To a solution of 1,4-dihydroxy anthraquinone (480 mg, 2 mmol) in acetone (30 mL) were added anhydrous potassium carbonate (1.1 g, 8 mmol) and 1,3 dibromopropane (1.21 g, 6 mmol) and the mixture was refluxed for 24 h. The progress of the reaction was monitored by TLC. After completion of the reaction, potassium carbonate was removed by filtration and the solvent was evaporated under reduced pressure to get the crude product. This was further purified by column chromatography (30% EtOAc-hexane) to afford the compound IIa as a yellow solid (791 mg, 82%).

$^1$H NMR ($CDCl_3$): δ 2.40-2.52 (m, 4H), 3.85-3.91 (t, 4H, J=6.51 Hz), 4.22-4.28 (t, 4H), J=5.53 Hz), 7.34 (s, 2H), 7.71-7.77 (m, 2H), 8.15-8.18 (m, 2H).

FABMS: 482 ($M^+$).

To a solution of 1,4-bis-(3-bromo propyloxy)-anthracene-9,10-dione (IIa) (482 mg, 1 mmol) in dry acetonitrile (30 mL) were added anhydrous $K_2CO_3$ (829 mg, 6 mmol) and (2S)-N-[4-hydroxy-5-methoxy-2-nitrobenzoyl]pyrrolidine-2-carboxaldehyde diethyl thioacetal (801 mg, 2mmol). The reaction mixture was refluxed for 24 h. After completion of reaction $K_2CO_3$ was removed by filtration and the solvent was evaporated under reduced pressure, the crude product was purified by column chromatography (80% EtOAc-hexane) to afford compound IIIa (807 mg, 72%).

$^1$H NMR ($CDCl_3$): δ 1.24-1.40 (m, 12H), 1.92-2.15 (m, 8H), 2.62-2.82 (m, 8H), 3.12-3.25 (m, 4H), 3.92 (s, 6H), 4.05-4.32 (m, 8H), 4.60-4.72 (m, 2H), 4.82 (d, 2H, J=3.66 Hz), 6.75 (s, 2H), 7.24 (s, 2H), 7.61-7.74 (m, 4H), 8.02-8.18 (m, 2H).

FABMS: 1121 ($M^+$).

The compound IIIa (1.121 g, 1 mmol) dissolved in methanol (40 mL) and added $SnCl_2.2H_2O$ (2.256 g, 10 mmol) was refluxed for 4 h. The reaction mixture was cooled and the methanol was evaporated under vacuum. The residue was carefully adjusted to pH 8 with saturated $NaHCO_3$ solution and then extracted with ethyl acetate (2×30 mL). The combined organic phase was washed with brine (15 mL), dried over anhydrous $Na_2SO_4$ and evaporated under vacuum to afford the amino diethyl thioacetal IVa as a yellow oil (895 mg, 82%) and directly used in the next step.

A solution of amino thioacetal 33a (1.19 g, 1 mmol), $HgCl_2$ (1.19 mg, 4.4 mmol) and $CaCO_3$ (480 mg, 4.8 mmol) in acetonitrile-water (4:1) was stirred slowly at rt for overnight, until TLC indicate the complete disappearance of starting material. The reaction mixture was diluted with ethyl acetate (30 mL) and filtered through a celite. The clear yellow organic supernatant was extracted with ethyl acetate (2×20 mL). The organic layer was washed with saturated $NaHCO_3$ (20 mL), brine (20 mL) and the combined organic phase was dried over anhydrous $Na_2SO_4$. The organic layer was evaporated under vacuum and the crude product was purified by column chromatography (15% MeOH-EtOAc) to afford the compound Va as a yellow solid (493 mg, 51%).

$^1$H NMR ($CDCl_3$): δ 1.96-2.05 (m, 4H), 2.20-2.50 (m, 8H), 3.55-3.85 (m, 6H), 3.92 (s, 6H), 4.20-4.32 (m, 4H), 4.42-4.52 (m, 4H), 6.85 (s, 2H), 7.22 (s, 2H), 7.40 (s, 2H), 7.52 (d, 2H, J=4.39 Hz), 7.65-7.71 (m, 2H), 8.02-8.15 (m, 2H).

FABMS: 968 ($M^++1$).

EXAMPLE 2

To a solution of 1,4-dihydroxy anthraquinone (480 mg, 2 mmol) in acetone (30 mL) were added anhydrous potassium carbonate (1.1 g, 8 mmol) and 1,3 dibromobutane (1.29 g, 6 mmol) and the mixture was refluxed for 24 h. The progress of the reaction was monitored by TLC. After completion of the reaction, potassium carbonate was removed by filtration and the solvent was evaporated under reduced pressure to get the crude product. This was further purified by column chromatography (30% EtOAc-hexane) to afford the compound IIb as a yellow solid (826mg, 81%).

$^1$H NMR ($CDCl_3$, 200 MHz) 1.25-1.40 (m, 6H), 1.72-2.42 (m, 6H), 2.70-2.8 (m, 4H), 3.15-3.30 (m, 2H), 3.60 (t, 2H, J=6.20 Hz), 3.95 (s, 3H), 4.20 (t, 2H, J=4.96 Hz), 4.60-4.75 (m, 1H), 4.82 (d, 1H, J=4.33 Hz), 6.78 (s, 1H), 7.68 (s, 1H).

To a solution of 1,4-bis-(3-bromo butyloxy)-anthracene-9, 10-dione (IIb) (510 mg, 1 mmol) in dry acetonitrile (30 mL) were added anhydrous $K_2CO_3$ (829 mg, 6 mmol) and (2S)-N-[4-hydroxy-5-methoxy-2-nitrobenzoyl]pyrrolidine-2-carboxaldehyde diethyl thioacetal (810 mg, 2mmol). The reaction mixture was refluxed for 24 h. After completion of reaction $K_2CO_3$ was removed by filtration and the solvent was evaporated under reduced pressure, the crude product was purified by column chromatography (80% EtOAc-hexane) to afford compound IIIb (805 mg, 70%).

$^1$H NMR (CDCl$_3$): δ 1.25-1.40 (m, 12H), 2.0-2.32 (m, 16H), 2.62-2.80 (m, 8H), 3.12-3.25 (m, 4H), 3.92 (s, 6H), 4.08-4.40 (m, 8H), 4.60-4.71 (m, 2H), 4.82 (d, 2H, J=3.62 Hz), 6.77 (s, 2H), 7.23 (s, 2H), 7.62-7.78 (m, 4H), 8.02-8.18 (m, 2H).

FABMS: 1150 [M+1]$^+$

The compound IIIb (1.15 g, 1 mmol) dissolved in methanol (40 mL) and added SnCl$_2$.2H$_2$O (2.256 g, 10 mmol) was refluxed for 4 h. The reaction mixture was cooled and the methanol was evaporated under vacuum. The residue was carefully adjusted to pH 8 with saturated NaHCO$_3$ solution and then extracted with ethyl acetate (2×30 mL). The combined organic phase was washed with brine (15 mL), dried over anhydrous Na$_2$SO$_4$ and evaporated under vacuum to afford the amino diethyl thioacetal IVb as a yellow oil (895 mg, 80%) and directly used in the next step.

A solution of amino thioacetal IVb (1.12 mg, 1 mmol), HgCl$_2$ (1.19 mg, 4.4 mmol) and CaCO$_3$ (480 mg, 4.8 mmol) in acetonitrile-water (4:1) was stirred slowly at rt for overnight, until TLC indicate the complete disappearance of starting material. The reaction mixture was diluted with ethyl acetate (30 mL) and filtered through a celite. The clear yellow organic supernatant was extracted with ethyl acetate (2×20 mL). The organic layer was washed with saturated NaHCO$_3$ (20 mL), brine (20 mL) and the combined organic phase was dried over anhydrous Na$_2$SO$_4$. The organic layer was evaporated under vacuum and the crude product was purified by column chromatography (15% MeOH-EtOAc) to afford the compound Vb as a yellow solid (517 mg, 52%).

$^1$H NMR (CDCl$_3$): δ 1.96-2.35 (m, 16H), 3.50-3.84 (m, 6H), 3.92 (s, 6H), 4.12-4.38 (m, 8H), 6.82 (s, 2H), 7.23 (s, 2H), 7.42 (s, 2H), 7.56 (d, 2H, J=4.39 Hz), 7.62-7.72 (m, 2H), 8.02-8.18 (m, 2H).

FABMS: 996 [M+1]$^+$

EXAMPLE 3

To a solution of 1,4-dihydroxy anthraquinone (480 mg, 2 mmol) in acetone (30 mL) were added anhydrous potassium carbonate (1.1 g, 8 mmol) and 1,3 dibromopentane (1.38 mg, 6 mmol) and the mixture was refluxed for 24 h. The progress of the reaction was monitored by TLC. After completion of the reaction, potassium carbonate was removed by filtration and the solvent was evaporated under reduced pressure to get the crude product. This was further purified by column chromatography (30% EtOAc-hexane) to afford the compound IIc as a yellow solid (904 mg, 84%).

$^1$H NMR (CDCl$_3$): δ 1.75-2.07 (m, 12H), 3.49 (t, 4H, J=6.59 Hz), 4.08 (t, 4H, J=6.13 Hz), 7.25 (s, 2H), 7.69-7.75 (m, 2H), 8.13-8.20 (m, 2H).

FABMS: 538 [M]$^+$

To a solution of 1,4-bis-(3-bromo pentyloxy)-anthracene-9,10-dione (IIc) (538 mg, 1 mmol) in dry acetonitrile (30 mL) were added anhydrous K$_2$CO$_3$ (829 mg, 6 mmol) and (2S)-N-[4-hydroxy-5-methoxy-2-nitrobenzoyl]pyrrolidine-2-carboxaldehyde diethyl thioacetal (801 mg, 2 mmol). The reaction mixture was refluxed for 24 h. After completion of reaction K$_2$CO$_3$ was removed by filtration and the solvent was evaporated under reduced pressure, the crude product was purified by column chromatography (80% EtOAc-hexane) to afford compound IIIc (824 mg, 70%).

$^1$H NMR (CDCl$_3$): δ 1.23-1.42 (m, 12H), 1.83-2.18 (m, 20H), 2.65-2.85 (m, 8H), 3.12-3.28 (m, 4H), 3.93 (s, 6H), 4.05-4.20 (m, 8H), 4.60-4.71 (m, 2H), 4.83 (d, 2H, J=3.66 Hz), 6.77 (s, 2H), 7.24 (s, 2H), 7.60-7.73 (m, 4H), 8:02-8.18 (m, 2H).

FABMS: 1178 [M+1]$^+$

The compound IIIc (1.18 g, 1 mmol) dissolved in methanol (40 mL) and added SnCl$_2$.2H$_2$O (2.256 g, 10 mmol) was refluxed for 4 h. The reaction mixture was cooled and the methanol was evaporated under vacuum. The residue was carefully adjusted to pH 8 with saturated NaHCO$_3$ solution and then extracted with ethyl acetate (2×30 mL). The combined organic phase was washed with brine (15 mL), dried over anhydrous Na$_2$SO$_4$ and evaporated under vacuum to afford the amino diethyl thioacetal IVc as a yellow oil (963 mg, 84%) and directly used in the next step.

A solution of amino thioacetal IVc (1.15 mg, 1 mmol), HgCl$_2$ (1.19 mg, 4.4 mmol) and CaCO$_3$ (480 mg, 4.8 mmol) in acetonitrile-water (4:1) was stirred slowly at rt for overnight, until TLC indicate the complete disappearance of starting material. The reaction mixture was diluted with ethyl acetate (30 mL) and filtered through a celite. The clear yellow organic supernatant was extracted with ethyl acetate (2×20 mL). The organic layer was washed with saturated NaHCO$_3$ (20 mL), brine (20 mL) and the combined organic phase was dried over anhydrous Na$_2$SO$_4$. The organic layer was evaporated under vacuum and the crude product was purified by column chromatography (15% MeOH-EtOAc) to afford the compound Vc as a yellow solid (522 mg, 51%).

$^1$H NMR (CDCl$_3$): δ 1.95-2.32 (m, 20H), 3.53-3.82 (m, 6H), 3.92 (s, 6H), 4.07-4.13 (m, 8H), 6.76 (s, 2H), 7.23 (s, 2H), 7.44 (s, 2H), 7.58 (d, 2H, J=4.40 Hz), 7.65-7.69 (m, 2H), 8.02-8.16 (m, 2H).

FABMS: 1024 [M+1]$^+$

Biological Activity

In vitro Cytotoxicity Against Human Cancer Cell Lines:

Cytotoxicity: Compounds Va-c have been evaluated for the primary anticancer activity in selected human cancer cell lines. The cytotoxicity data for some representative compounds is shown in Table 1. For each compound, dose response curves against each cell line were measured at a minimum of five concentrations at 10 fold dilutions. A protocol of 48 h continuous drug exposure was used and a sulforhodamine B (SRB) protein assay was used to estimate cell viability or growth. The concentration causing 50% cell growth inhibition compared with the control has been calculated.

TABLE 1

In vitro cytotoxicity of compounds Va-c

| Compound | IC50[a] μM | | | | | | |
|---|---|---|---|---|---|---|---|
| | Hop62 | SiHa | MCF7 | Colo205 | PC3 | ZR-75-1 | A2780 |
| Va | <1.0 | 0.8 | 0.6 | <1.0 | 0.6 | 0.5 | 0.6 |
| Vb | — | 9.0 | 9.0 | 10 | 7.0 | — | 10.0 |
| Vc | 1.4 | 0.8 | 1.2 | <1.0 | 1.0 | 1.5 | 0.6 |

[a]Dose of compound required to inhibit cell growth by 50% compared to untreated cell controls The comparison of the data of Table 1 reveals the importance of the alkane spacer. The 3 carbon spacer of compound Va confers a suitable fit in the minor groove of double helix DNA and shows slightly higher activity in this series of compounds.

What is claimed is:

1. A compound of the formula Va-c:

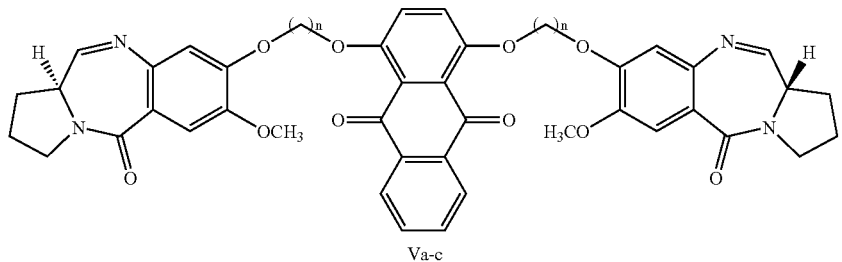

wherein n is 3, 4 or 5; or a salt thereof.

2. A pharmaceutical composition comprising at least one compound according to claim 1, or a pharmaceutically acceptable salt thereof, optionally with a pharmaceutically acceptable carrier, adjuvant, or additive.

3. A process for the preparation of a compound of formula Va-c:

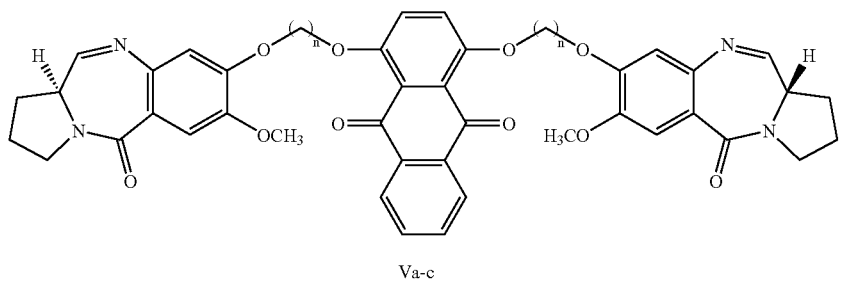

wherein n is 3, 4 or 5; or a salt thereof, comprising the steps of:

a. reacting 1,4-dihydroxy anthraquinone of formula I with a dibromoalkane, in an aprotic water miscible organic solvent, in the presence of a mild inorganic base, at refluxing temperature, for a period of about 24 hours, followed by removing the inorganic base by filtration and removing the organic solvent by evaporation, under reduced pressure, to obtain a 1,4-bis-(n-bromo alkoxy)-anthracene-9,10-dione of formula IIa-c,

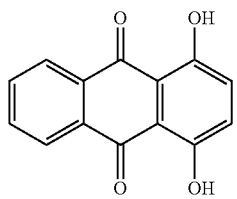

-continued

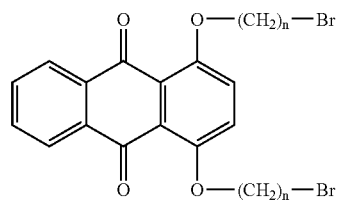

wherein n is 3, 4 or 5;

b. reacting the 1,4-bis-(n-bromo alkoxy)anthracene-9,10-dione of formula IIa-c with (2S)-N-[4-hydroxy-5-methoxy-2-nitrobenzoyl]pyrrolidine-2-carbox aldehyde diethyl thioacetal in a dry organic solvent, in the presence of a mild inorganic base, at refluxing temperature, for a period of about 24 hours, followed by removing the inorganic base by filtration and removing the organic solvent by evaporation, under reduced pressure, to obtain a 1,4-bis-{n-[(2S)-N-(4-oxy-5-methoxy-2-nitrobenzoyl)pyrrolidine-2-carboxaldehyde diethyl thioacetal]alkyloxy}-anthracene-9,10-dione of formula IIIa-c, organic layer, followed by purifying the crude product to obtain the desired compound of formula Va-c; or a salt thereof.

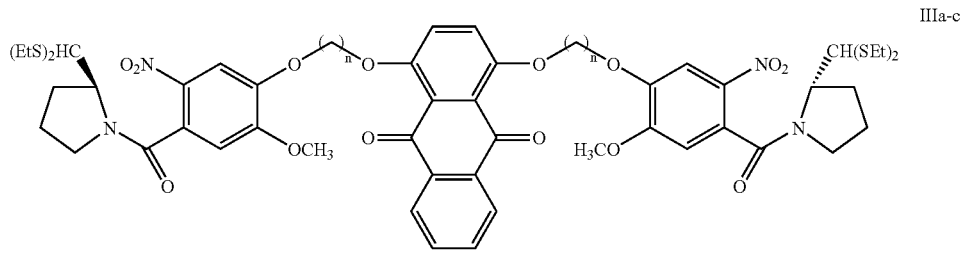

IIIa-c wherein n is 3, 4 or 5;

c. reducing the 1,4-bis-{n-[(2S)-N-(4-oxy-5-methoxy-2-nitrobenzoyl)pyrrolidine-2-carboxaldehyde diethyl thioacetal]alkyloxy}-anthracene-9,10-dione of formula IIIa-c with tin chloride, in an alcoholic solvent, under reflux, for a period of about 4 hours, cooling the resultant reaction reaction mixture to a temperature of 20-25° C., and removing the excess alcohol by evaporation and adjusting the residue to a pH of about 8 with an inorganic base, followed by extracting the residue with ethyl acetate and washing the combined organic ethyl acetate phase with brine solution, followed by evaporating ethyl acetate to obtain an amino thioacetal 1,4-bis-{n-[(2S)-N-(4-oxy-5-methoxy-2-aminobenzoyl)pyrrolidine-2-carboxaldehyde diethyl thioacetal]alkyloxy}-anthracene-9,10-dione of formula IVa-c,

4. A process as claimed in claim 3, wherein the mild inorganic base used in steps (a) and (b) is potassium carbonate.

5. A process as claimed in claim 3, wherein the dibromoalkane used in step (a) is selected from the group consisting of 1,3-dibromopropane, 1,4-dibromobutane, and 1,5-dibromopentane.

6. A process as claimed in claim 3, wherein the aprotic organic solvent used in step (a) is acetone or acetonitrile.

7. A process as claimed in claim 3, wherein the organic solvent used in step (b) is selected from the group consisting of acetonitrile, acetone and DMF.

8. A process as claimed in claim 3, wherein the alcohol used in step (c) is methanol or ethanol.

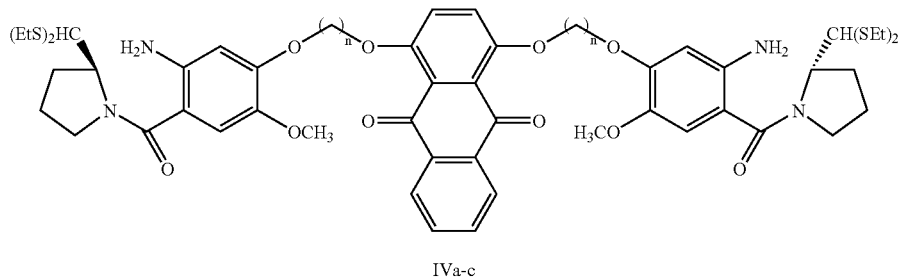

IVa-c wherein n is 3, 4 or 5; and d. reacting the amino thioacetal amino thioacetal 1,4-bis-{n-[(2S)-N-(4-oxy-5-methoxy-2-aminobenzoyl)pyrrolidine-2-carboxaldehyde diethyl thioacetal]alkyloxy}anthracene-9,10-dione of formula IVa-c with mercuric chloride in a mixture of water and acetonitrile, in the presence of and calcium carbonate, under stirring, for a period of about 8-10 hours, at a temperature in the range of 25-30° C. and diluting the mixture with ethyl acetate, followed by filtering and extracting the mixture with ethyl acetate, washing the resultant organic phase with sodium bicarbonate and brine, and evaporating the

9. A compound according to claim 1, wherein the compound is 1,4-bis-{3-[7-methoxy-8-oxy-(11aS)-1,2,3,11a-tetrahydro-5H-pyrrolo[2,1-c][1,4]benzodiazepin-5-one]propyloxy}anthracene-9,10-dione, or a salt thereof.

10. A compound according to claim 1, wherein the compound is 1,4-bis-{4-[7-methoxy-8-oxy-(11aS)-1,2,3,11a-tetrahydro-5H-pyrrolo[2,1-c][1,4]benzodiazepin-5-one]butyloxy}anthracene-9,10-dione, or a salt thereof.

11. A compound according to claim 1, wherein the compound is 1,4-bis-{5-[7-methoxy-8-oxy-(11aS)-1,2,3,11a-tetrahydro-5H-pyrrolo[2,1-c][1,4]benzodiazepin-5-one]pentyloxy}anthracene-9,10-dione, or a salt thereof.

* * * * *